United States Patent [19]
Krafft et al.

[11] Patent Number: 5,980,936
[45] Date of Patent: Nov. 9, 1999

[54] MULTIPLE EMULSIONS COMPRISING A HYDROPHOBIC CONTINUOUS PHASE

[75] Inventors: Marie-Pierre Krafft; Jean G. Riess, both of Nice, France; Leila Zarif, Annandale, N.J.

[73] Assignee: Alliance Pharmaceutical Corp., San Diego, Calif.

[21] Appl. No.: 08/908,821

[22] Filed: Aug. 7, 1997

[51] Int. Cl.$^6$ .............................. A61K 9/127; A61K 9/66
[52] U.S. Cl. .................... 424/450; 424/455; 514/937; 514/938; 514/948
[58] Field of Search .................................. 424/455, 458, 424/450; 514/937, 938, 943

[56] References Cited

U.S. PATENT DOCUMENTS

| 3,828,085 | 8/1974 | Price et al. ............................. 260/404.5 |
| 3,975,512 | 8/1976 | Long, Jr. ...................................... 424/5 |
| 5,114,703 | 5/1992 | Wolf et al. .................................... 424/5 |
| 5,304,325 | 4/1994 | Kaufman et al. ....................... 252/312 |
| 5,350,571 | 9/1994 | Kaufman et al. ............................ 424/9 |
| 5,514,720 | 5/1996 | Clark et al. ............................... 514/749 |
| 5,733,526 | 3/1998 | Trevino et al. ......................... 424/9.52 |
| 5,851,539 | 12/1998 | Mellul et al. ........................... 424/401 |

FOREIGN PATENT DOCUMENTS

| 0 255 443 | 2/1988 | European Pat. Off. . |
| 0 311 473 | 4/1989 | European Pat. Off. . |
| 0 559 013 | 9/1993 | European Pat. Off. . |
| 0 782 846 | 7/1997 | European Pat. Off. . |
| 2 665 705 | 2/1992 | France . |
| 2677360 | 12/1992 | France . |
| 2 679 150 | 1/1993 | France . |
| 2 694 599 | 2/1994 | France . |
| 44 05 627 | 8/1995 | Germany . |
| WO 90/15807 | 12/1990 | WIPO . |
| WO 94/14415 | 7/1994 | WIPO . |
| WO 95/09606 | 4/1995 | WIPO . |
| WO 95/33447 | 12/1995 | WIPO . |
| WO 96/35411 | 11/1996 | WIPO . |

OTHER PUBLICATIONS

Grenier, et al. "Fluorinated Surfactants Intended for Biomedical Uses" *Organofluorine Compounds in Medicinal Chemistry and Biomedical Applications*, R. Filler, eds. pp. 339–379 (1993 Elsevier Science Publishers B.V.).

Safwat, et al. "The Formulation–Performance Relationship of Multiple Emulsions and Ocular Activity" J. of Controlled Release 32: 259–268 (1994).

*Primary Examiner*—Thurman K. Page
*Assistant Examiner*—Lakshmi Channavajjala
*Attorney, Agent, or Firm*—Knobbe, Martens, Olson & Bear, LLP

[57] ABSTRACT

Multiple emulsions comprising a discontinuous emulsified phase incorporating a highly polar liquid, a second component selected from the group consisting of fluorocarbons and hydrocarbons and a continuous hydrophobic phase are disclosed. In preferred embodiments, the hydrophobic phase may comprise a fluorocarbon or hydrocarbon. Additionally, the stable multiple emulsions of the present invention may further incorporate a bioactive agent and are particularly suitable for drug delivery including pulmonary drug delivery.

30 Claims, No Drawings

MULTIPLE EMULSIONS COMPRISING A HYDROPHOBIC CONTINUOUS PHASE

FIELD OF THE INVENTION

The present invention relates to multiple emulsions comprising a discontinuous emulsified phase incorporating a highly polar component and a fluorocarbon or hydrocarbon and a hydrophobic continuous phase. In preferred embodiments, the compositions of the present invention may further incorporate a bioactive agent.

BACKGROUND OF THE INVENTION

The efficacy of many bioactive agents is predicated on their ability to proceed to the selected target sites and remain present in effective concentrations for sufficient periods of time to accomplish the desired therapeutic or diagnostic purpose. Difficulty in achieving efficacy may be exacerbated by the location and environment of the target site as well as by the inherent physical characteristics of the compound administered. For example, drug delivery via routes that are subject to repeated drainage or flushing as part of the body's natural physiological functions offers significant impediments to the effective administration and controlled release of bioactive agents. In this respect, delivery and retention problems are often encountered when administering compounds through the respiratory or gastrointestinal tracts. Repeated administration of fairly large doses are often required to compensate for the amount of drug washed away and to maintain an effective dosing regimen when employing such routes. Moreover, the molecular properties of the bioactive compound may impair the absorption through a given delivery route, thereby resulting in a substantial reduction in efficacy. This is particularly true of lipophilic compounds that are not soluble in aqueous environments (i.e. they are hydrophobic). For instance, insoluble particulates are known to be subject to phagocytosis and pinocytosis, resulting in the accelerated removal of the compound from the target site. Such reductions in delivery and retention time complicate dosing regimes, waste bioactive resources and generally reduce the overall efficacy of the administered drug.

Unlike many hydrophilic compounds, the delivery of lipid soluble or lipophilic drugs by conventional means has been and continues to be problematic. Unfortunately, a number of the most promising therapeutic and diagnostic agents currently under development are relatively insoluble in water. Some are bulky polycyclic molecules whose substantial physical size, coupled with the intrinsic lipophilicity of their molecular structure, has severely limited their use in practical bioactive applications. For instance, the oral administration of lipophilic agents using conventional tablets and capsules suffers the disadvantage of a variable rate of absorption and depends on factors such as the presence or absence of food, the pH of gastrointestinal fluids and gastric emptying rates. Moreover, the degradation of labile drugs by gastric fluids and drug metabolizing enzymes may reduce the drug bioavailability to the point of therapeutic failure.

Other delivery routes fare little better when lipophilic (i.e. hydrophobic) compounds are administered using conventional delivery vehicles. Administration of these water insoluble drugs often requires that they be formulated in the form of hydrocarbon oil in water emulsions or that they be solubilized into a water miscible phase. This suffers drawbacks associated with the formulation of a suitably stable dosage form. For example, the current method used for the intravenous administration of the highly lipophilic cancer drug Taxol involves the use of a polyoxyethylated castor oil vehicle that has been associated with hypersensitivity reactions including dyspnea, bronchospasm, urticaria, and hypotension. In addition, the intravenous administration of drugs such as Taxol, which exhibit high systemic toxicities, severely limits their therapeutic capacity. Thus, despite encouraging results with existing delivery systems, the inherently low bioavailability of these lipophilic compounds at the target site due to inefficient or toxic delivery systems substantially reduces their efficacy.

In spite of the difficulties associated with the delivery of lipophilic drugs, the potential advantages in developing methods to do so are great. Extensive work has been done to show that the membrane permeability, bioavailability and efficacy of drugs often increases with increasing lipophilicity. The development of new systems for the delivery and prolonged release of these compounds could, therefore, significantly increase therapeutic efficacy for the treatment of a wide variety of indications.

In this respect, one class of delivery vehicles that has shown great promise when used for the administration of bioactive agents is fluorochemicals. During recent years, fluorochemicals have found wide ranging application in the medical field as therapeutic agents. The use of fluorochemicals to treat medical conditions is based, to a large extent, on the unique physical and chemical properties of these substances. In particular, the relatively low reactivity of fluorochemicals allows them to be combined with a wide variety of compounds without altering the properties of the incorporated agent. This relative inactivity, when coupled with other beneficial characteristics such as an ability to carry substantial amounts of oxygen, radioopaqueness for certain fluorochemicals and forms of radiation as well as low surface energies, have made fluorochemicals invaluable for a number of therapeutic and diagnostic applications.

For example, various fluorochemical emulsions have been used as oxygen carriers during medical procedures. Conventional fluorochemical-in-water emulsions, which may be infused directly into the blood stream, consist of a selected fluorochemical dispersed in the form of droplets in a continuous aqueous phase. Because of the high oxygen-carrying capacity of fluorochemicals, such emulsions are particularly useful as blood substitutes to provide oxygen to the vascular system. Fluosol® (Green Cross Corp., Osaka, Japan), a formerly commercially available emulsion containing fluorochemicals, has been used as a gas carrier to oxygenate the myocardium during percutaneous transluminal coronary angioplasty. Fluorochemicals have also been used as contrast enhancement media in radiological imaging (U.S. Pat. No. 3,975,512) and in nuclear magnetic resonance imaging (U.S. Pat. No. 5,114,703). A fluorochemical emulsion is currently being investigated as a means of expanding the efficacy of perioperative hemodilution and reducing the need for homologous blood transfusion. Other proposed medical uses include the treatment of cardiovascular and cerebrovascular diseases, organ preservation and cancer therapy; diagnostic ultrasound imaging and veterinary therapy.

In addition to traditional fluorochemical-in-water emulsions, other fluorochemical systems have been examined for utility under a variety of conditions. For example, it has been shown that water-in-fluorochemical reverse emulsions may be stabilized through the selection of appropriate emulsifiers and used as drug delivery vehicles. Such systems have been reported as being useful.

Yet, despite these advancements there still remains a substantial need for delivery vehicles that may be used for the effective administration of hydrophobic bioactive agents. Similarly, it is often desirable to administer both hydrophobic and hydrophilic compounds simultaneously using the same vehicle comprising a hydrophobic continuous phase.

Accordingly, it is an object of the present invention to provide multiple emulsions capable of incorporating therapeutic or diagnostic compounds which exhibit improved shelf-lives and stability.

It is a further objective of the present invention to provide bioactive preparations capable of simultaneously delivering both lipophilic and hydrophilic bioactive agents while allowing improved control over release of both compounds.

It is yet a further objective of the present invention to provide methods for the formation and delivery of multiple emulsions comprising bioactive agents exhibiting enhanced bioavailability.

SUMMARY OF THE INVENTION

The present invention accomplishes these and other objectives by providing unique multiple emulsions which may be used for the administration of bioactive agents. In preferred embodiments, the invention comprises multiple emulsions having a continuous hydrophobic phase and a discontinuous emulsified phase. That is, the discontinuous phase of the disclosed multiple emulsions comprises an emulsified phase incorporating a polar liquid (W) and a second component selected from the group of hydrocarbons (HC) and fluorocarbons (FC). By "emulsified" it is meant that the two components (either W and HC or W and FC) are subjected to sufficient energy, preferably in the presence of a first dispersant, to provide a substantially homogeneous suspension of an immiscible liquid in a continuous liquid carrier. In accordance with the teachings herein, the discontinuous emulsified phase may comprise a W-in-FC emulsion, a W-in-HC emulsion, a FC-in-W emulsion or a HC-in-W emulsion. The selected emulsion is then dispersed in a continuous hydrophobic phase, preferably in the presence of a second dispersant, to provide stable multiple emulsions for the delivery of bioactive agents. Preferably, the continuous hydrophobic phase comprises a liquid hydrophobic compound selected from the group consisting of hydrocarbons and fluorocarbons.

It should be appreciated that the discontinuous emulsified phase preferably comprises two distinct phases of one immiscible liquid dispersed in another. By immiscible it is meant than one liquid is at least partially insoluble in the other liquid. As set forth above, one of the phases making up the emulsified phase is a polar liquid while the other is selected from the group consisting of hydrocarbons and fluorocarbons. In preferred embodiments the polar liquid will be aqueous or aqueous based. However, other polar liquids such as, for example, alcohols, alkyl sulfoxides and combinations thereof may be compatible with the present invention. In particular short chain alcohols (i.e. carbon chain length ≦4 carbons) and alkyl sulfoxides such as dimethylsulfoxide may be suitable for use with or without the addition of water. As such, the terms "aqueous" and "polar liquid" may be used interchangeably throughout the instant specification unless the context of the passage indicates differently. The letter W shall be held to mean any polar liquid including aqueous solutions.

In any case those skilled in the art will appreciate there is a distinct first interface separating the two components of the discontinuous emulsified phase. Preferably the first dispersant is largely deposited at the first interface to stabilize the emulsified phase and allow it to maintain its distinct homogenous configuration when it is dispersed in the hydrophobic continuous phase of the multiple emulsions.

In this regard, dispersion of the discontinuous emulsified phase in the hydrophobic continuous phase provides the multiple emulsions of the present invention. Preferably, the multiple emulsions further comprise a second dispersant largely deposited at the interface between the discontinuous emulsified phase and the continuous hydrophobic phase. As indicated above, the continuous hydrophobic phase may comprise either a hydrocarbon or a fluorocarbon.

As used herein, the term "dispersant" shall be held to mean any single surfactant, emulsifying agent or surfactant system that is capable of reducing the interfacial tension between distinct phases. It will be appreciated that the first and second dispersants used in the disclosed multiple emulsions may be the same or different.

Accordingly, in keeping with the teachings herein the multiple emulsions of the invention may comprise W-in-FC-in-HC emulsions, FC-in-W-in-HC emulsions, HC-in-W-in-FC emulsions and W-in-HC-in-FC emulsions. Consistent with the scope of the instant disclosure, the hydrocarbon or fluorocarbon of the continuous hydrophobic phase may be the same or different than the hydrocarbon or fluorocarbon incorporated in the discontinuous emulsified phase. Similarly, the first dispersant may be the same or different than the second dispersant. In any case, the multiple emulsions may be combined with bioactive agents to provide stable bioactive multiple emulsions having extended shelf-lives, enhanced bioavailability and prolonged delivery profiles.

Accordingly, one aspect provided by the present invention are stable multiple emulsions for the delivery of bioactive agents comprising:

a discontinuous emulsified phase comprising a first dispersant a polar liquid and a second component selected from the group consisting of fluorocarbons and hydrocarbons;

a continuous phase comprising a liquid hydrophobic compound; and an effective dispersing amount of a second dispersant wherein said discontinuous emulsified phase is immiscible in said liquid hydrophobic compound.

In preferred embodiments the discontinuous emulsified phase will comprise an FC-in-W emulsion, a W-in-FC emulsion, a HC-in-W emulsion or a W-in-HC emulsion. Moreover, the continuous hydrophobic phase is selected from the group consisting of hydrocarbons and fluorocarbons. Of course those skilled in the art will appreciate that the disclosed multiple emulsions may further comprise effective dispersing amounts of a first and second dispersants and at least one bioactive agent.

A wide variety of hydrocarbons and hydrocarbon derivatives may be used to form the preparations of the present invention. As used herein, the term "hydrocarbon" is held to mean any compound, including bioactive agents, which are capable of being dispersed in, or of dispersing, the other disclosed components of the multiple emulsions. That is, the hydrocarbon itself may be a bioactive agent or drug although non-bioactive hydrocarbons are compatible with the teachings herein. In any case, the selected hydrocarbon is preferably biocompatible and readily available from natural or synthetic sources.

Hydrocarbons compatible with the present invention include saturated or unsaturated hydrocarbons (cyclic, aliphatic or aromatic), or hydrocarbon derivatives including substituted and unsubstituted compounds (e.g. alcohols, aldehydes, ketones, amines, ethers, amides, etc.). Lipophilic bioactive compounds that may be incorporated using the disclosed dispersing agents, such as selected steroidal compounds, aminoglycosidic compounds and cholesterol derivatives are also hydrocarbons for the purposes of the invention. Yet other compatible hydrocarbons include paraffins, lipids, waxes, glycerides, fatty acids, natural and synthetic hydrocarbons and derivatives thereof. Preferred natural hydrocarbons may be selected from the group consisting of canola oil, soybean oil, olive oil, corn oil, castor oil, safflower oil and sunflower oil.

Similarly it will be appreciated that the term "fluorocarbon" is used in a broad sense and comprises any highly fluorinated compound such as a linear, branched, cyclic, saturated or unsaturated fluorinated hydrocarbon, optionally containing at least one heteroatom and/or bromine or chlorine atom, wherein at least 30% of the hydrogen atoms of said hydrocarbon compound have been replaced by fluorine atoms. Particularly preferred embodiments comprise perfluorocarbons. Fluorocarbons compatible with the present invention are generally selected for beneficial physical characteristics such as low toxicity, low surface tension, high spreading coefficient and the ability to transport gases.

The multiple emulsions of the present invention may be formed using conventional emulsification procedures well known to those skilled in the art. In this regard it will be appreciated that the desired multiple emulsions can be formed using ultrasound, microfluidization, high pressure homogenization or any other appropriate method. Preferably, a two step process is used wherein the discontinuous emulsified phase is formed and then dispersed in the continuous hydrophobic phase. In such cases the energy imparted during the second step is preferably such that it does not substantially disrupt the emulsion formed during the first step.

Accordingly, another aspect of the invention is directed to methods for forming a stable multiple emulsion comprising the steps of:
 emulsifying a first dispersant a polar liquid and a second component selected from the group consisting of fluorocarbons and hydrocarbons to provide an emulsified disperse phase; and
 dispersing said emulsified disperse phase in a continuous phase comprising a hydrophobic compound and an effective dispersing amount of a second dispersant wherein said emulsified disperse phase is immiscible in said hydrophobic compound.

In preferred embodiments incorporated dispersants are selected from non-fluorinated surfactants and fluorinated surfactants. As previously alluded to, the included dispersants may be the same or different depending on the selected emulsion components and the desired configuration of the multiple emulsion. Of course those skilled in the art will appreciate that any dispersant or dispersants which provide the desired multiple emulsion may be incorporated in the preparations of the present invention. The first dispersant, deposited at the first interface (between the W and HC or FC) in the discontinuous emulsified phase often, but not necessarily has a high hydrophilic-lipophilic balance (HLB). Preferably the first dispersant is selected from the group consisting of phospholipids, poloxamers (such as pluronics), poloxamines (such as tetronics) and sorbitan esters. In particularly preferred embodiments the first dispersant is a phospholipid or combination of phospholipids such as egg yolk phospholipid (EYP).

The second dispersant, optionally deposited at the interface between the discontinuous emulsified phase and the continuous hydrophobic phase, may also be a non-fluorinated surfactant. This is particularly preferred when the discontinuous phase exhibits an aqueous exterior so the second interface is between the aqueous component and the hydrophobic continuous phase. Conversely, when the discontinuous emulsified phase exhibits a HC or FC exterior (i.e. in a W-in-FC-in-HC emulsion), fluorinated surfactants are preferred. In such embodiments, the second dispersant may be selected from the group consisting of semi-fluorinated alkanes or alkenes and perfluoroalkylated surfactants. In particularly preferred embodiments, the dispersing agent is selected from the group consisting of diblock compounds having a fluorinated region and a hydrogenated region. In other preferred embodiments, the second dispersant may be selected from fluorinated surfactants such as those described in "Fluorinated Surfactants Intended for Biomedical Uses," J. Greiner, J. G. Riess and P. Vierling in *Organofluorine Compounds in Medical Chemistry and Biomedical Applications*, R. Filler, T. Kobayashi and Y. Yagupolski (eds.), Elsevier, 339–380 (1993).

In yet another aspect, the present invention provides methods for delivering a bioactive agent to a patient using the disclosed multiple emulsions. As used herein, the term bioactive agent is defined to mean any pharmaceutical compound or composition, including diagnostic and therapeutic agents as well as physiologically acceptable gases such as oxygen or nitric oxide, which may be administered to an animal to treat a disorder or disease. In general the methods comprise:
 providing a bioactive multiple emulsion comprising an discontinuous emulsified phase having therein a first dispersant a polar liquid and a second component selected from the group consisting of fluorocarbons and hydrocarbon oils, said emulsified phase dispersed in a continuous phase comprising a hydrophobic compound and an effective dispersing amount of a second dispersant wherein said bioactive multiple emulsion further comprises at least one bioactive agent; and
 administering said bioactive multiple emulsion to a patient.

In accordance with the teachings herein the bioactive preparations of the present invention may be administered to a patient using a route of administration selected from the group consisting of topical, subcutaneous, pulmonary, synovial, intramuscular, intraperitoneal, nasal, vaginal, rectal, aural, oral and ocular routes. Due to the physical characteristics of the bioactive multiple emulsions (i.e. the hydrophobic continuous phase comprising either a HC or FC), pulmonary administration (when FC) and administration to the gastrointestinal tract (when HC and FC) of these preparations is particularly preferred.

Pharmaceutically effective amounts of both lipophilic bioactive agents and those which are soluble in water may be advantageously delivered using the preparations of the present invention. Preferably, water soluble bioactive agents are delivered in combination with a lipophilic or hydrophobic agent although single bioactive agents may also be delivered effectively. In each of the aforementioned embodiments, bioactive agents compatible with the present invention include, but are not limited to, respiratory agents, bronchodilators, bronchoconstrictors, antibiotics, antivirals, mydriatics, antiglaucomas, anti-inflammatories, antihistaminics, antineoplastics, anesthetics, ophthalmic agents, enzymes, cardiovascular agents, polynucleotides, genetic material, viral vectors, immunoactive agents, imaging agents, immunosuppressive agents, peptides, proteins, physiological gases, gastrointestinal agents and combinations thereof.

Pharmaceutically effective amounts of the selected bioactive agents may be determined using techniques well known in the art. Additional, stabilizers, solubilizing agents or co-solvents such as, for example, natural and synthetic polymers, diblocks, polyethylene glycol, sorbitan esters poloxamers such as pluronics or poloxamines can be used to facilitate the incorporation of the selected bioactive agents or agents into one or the other phase of the preparation. It will further be appreciated that the bioactive agents may be incorporated in the form of relatively insoluble solid particulates or associated with insoluble polymeric particulates.

Other objects, features and advantages of the present invention will be apparent to those skilled in the art from a consideration of the following detailed description of preferred exemplary embodiments.

DETAILED DESCRIPTION OF THE INVENTION

In a broad aspect the present invention provides multiple emulsions that may be used for controlled administration of bioactive agents. Preferred embodiments of the present invention comprise a discontinuous emulsified disperse phase and a continuous phase comprising a hydrophobic compound. The discontinuous emulsified phase, which is preferably in the form of a homogeneous suspension or dispersion, comprises a polar liquid and a second component selected from the group of hydrocarbons and fluorocarbons. The discontinuous emulsified phase is further dispersed, as a discrete entity, into the continuous phase. That is, the multiple emulsions of the inventions comprise three distinct, relatively immiscible phases, two of which are present in the discontinuous emulsified phase. The preparations are preferably stabilized by one or more dispersants which are, to a large extent, deposited at the interfaces between the polar liquid and second component of the discontinuous emulsified phase and at the interface between the emulsified phase and the continuous phase. The dispersants are preferably hydrogenated or fluorinated surfactants.

In selected embodiments the multiple emulsions comprise a hydrophobic continuous phase comprising a hydrocarbon or a fluorocarbon. These embodiments, each comprising various discontinuous emulsified phases, have utility as vehicles and controlled release systems for bioactive agents and, more generally lipophilic, hydrophilic or amphiphilic material. More particularly, with the multiple emulsions of the present invention the diffusion of a bioactive agent, including both lipophilic and hydrophilic compounds, may be significantly retarded by the various shells and interfaces of the preparations. These properties allow for controlled drug release and prolonged delivery profiles, particularly for lipophilic bioactive agents. The barriers provided by the multiple emulsions can also act to protect encapsulated substances from body fluids and vice-versa, thereby reducing the toxicity of such compounds.

It should be appreciated that the discontinuous emulsified phase will constitute a discrete, homogeneous droplets dispersed in the hydrophobic continuous phase. These discrete droplets will, in turn, comprise an emulsion or reverse emulsion depending on whether the second component (i.e. a HC or FC) is dispersed in the polar liquid or whether the polar liquid is dispersed in the second component. As described herein the discontinuous emulsified phase may therefore comprise a FC-in-W emulsion, a W-in-FC emulsion, a HC-in-W emulsion or a W-in-HC emulsion. These emulsions may further be dispersed in a hydrocarbon continuous phase or a fluorocarbon continuous phase. As such, the multiple emulsions may comprise a W-in-FC-in-HC multiple emulsion, a FC-in-W-in-HC multiple emulsion, a W-in-HC-in-FC multiple emulsion or a HC-in-W-in-FC multiple emulsion. A dispersant or dispersants may be included to stabilize each of the aforementioned multiple emulsions which can further include at least one bioactive agent.

As indicated above, the multiple emulsions of the present invention exhibit superior delivery characteristics. Specifically, it is believed that some or all of the incorporated bioactive agents may be compartmentalized in one of the discrete particulates of the discontinuous emulsified phase. The encapsulation or coating of some or all of the bioactive agent appears to retard diffusion of the bioactive agent or agents into the aqueous physiological environment where it would be subject to degradation.

Those skilled in the art will appreciate that the same fluorocarbons and hydrocarbons may comprise the second component of the discontinuous emulsified phase and the continuous hydrophobic phase. That is, in one embodiment a selected hydrocarbon could be used to form the continuous hydrophobic phase while in another embodiment the same hydrocarbon could be used in the dispersed emulsified phase. Similarly, the disclosed fluorocarbons may be used in either role depending on the embodiment selected. As such, the following discussion regarding hydrocarbons and fluorocarbons will be generally applicable to all embodiments of the invention without limitation as to the site of incorporation of the specific compound within the multiple emulsion.

In the multiple emulsions of the present invention, the absolute concentration of the hydrocarbon or fluorocarbon will, to some extent, depend on whether it is to be incorporated as the continuous hydrophobic phase or as the second component within the discontinuous emulsified phase. When used in the continuous phase, the selected HC or FC may comprise from about 5% to about 99.5% (v/v) of the multiple emulsion and more preferably from about 50% to about 95% (v/v) and even more preferably from about 70% to about 90% (v/v). Conversely, when incorporated in the dicontinuous emulsified phase the FC or HC may comprise from about 0.1% to about 75% (v/v) of the multiple emulsion and more preferably from about 1% to about 40% (v/v) and even more preferably from about 5% to about 25% (v/v).

The fluorocarbons (i.e. highly fluorinated or perfluorinated organic compounds) comprising the continuous hydrophobic phase or the second component of the discontinuous emulsified phase are preferably chosen for their low toxicity, surface tension and spreading coefficient. Particularly preferred fluorochemicals will be capable of delivering therapeutically significant amounts of gases including nitric oxide or oxygen. In general, the highly fluorinated or perfluorinated compounds may be linear, branched or cyclic, saturated or unsaturated fluorinated compounds. Conventional structural derivatives of these fluorochemicals are also contemplated as being within the scope of the present invention as well. In addition, these totally or partially fluorinated compounds may contain one or more hetero atoms and/or atoms of bromine or chlorine. The term "partially fluorinated" indicates that at least 30% of the hydrogen atoms in the hydrocarbon oil or derivative thereof have been replaced with fluorine atoms. Preferably, these fluorochemicals comprise from 2 to 20 carbon atoms and include, but are not limited to, linear, cyclic or polycyclic perfluoroalkanes, bis(perfluoroalkyl)alkenes, perfluoroethers, perfluoropolyethers, perfluoroamines, perfluoroalkyl bromides and perfluoroalkyl chlorides. The aforementioned compounds, as well as those discussed below may be used either alone or in combination.

In a preferred embodiment of the invention the incorporated fluorinated compound comprises perfluorooctyl bromide, $C_8F_{17}Br$ (PFOB or perflubron), perfluorooctylethane $C_8F_{17}C_2H_5$ (PFOE) or of perfluorodecylethane $C_{10}F_{21}C_2H_5$ (PFDE). Other preferred fluorochemicals include perfluoroctane $C_8F_{18}$, perfluorodecane $C_{10}F_{22}$, perfluorodecyl bromide $C_{10}F_{21}Br$ (PFDB) or perfluorodecalin (FDC).

In addition to the aforementioned compounds, exemplary fluorochemicals which are specifically contemplated for use in the present invention generally include halogenated fluorochemicals (i.e. $C_nF_{2n+1}X$, $XC_nF_{2n}X$, where n=2–10, X=Br, Cl or l) and, in particular, 1-bromo-F-butane n-$C_4F_9Br$, 1-bromo-F-hexane (n-$C_6F_{13}Br$), 1-bromo-F-heptane (n-$C_7F_{15}Br$), 1,4-dibromo-F-butane and 1,6-dibromo-F-hexane. Other useful brominated fluorochemicals are disclosed in U.S. Pat. No. 3,975,512 to Long and are incorporated herein by reference.

Specific fluorochemicals having chloride substituents, such as perfluorooctyl chloride (n-$C_8F_{17}Cl$), 1,8-dichloro-F-octane (n-$ClC_8F_{16}Cl$), 1,6-dichloro-F-hexane (n-$ClC_6F_{12}Cl$), and 1,4-dichloro-F-butane (n-$ClC_4F_8Cl$) are also preferred.

Fluorocarbons, fluorocarbon-hydrocarbon compounds and halogenated fluorochemicals containing other linkage groups, such as esters, thioethers, ethene groups and amines are also suitable for use in forming the compositions of the present invention. For instance, compounds having the general formula, $C_nF_{2n+1}OC_mF_{2m+1}$, or $C_nF_{2n+1}CH=CHC_mF_{2m+1}$, (as for example $C_4F_9CH=CHC_4F_9$ (F-44E), i-$C_3F_9CH=CHC_6F\_$ (F-i36E), and $C_6F_{13}CH=CHC_6F_{13}$ (F-66E)) where n and m are the same or different and n and m are integers from about 2 to about 12 are compatible with teachings herein. Useful fluorochemical-hydrocarbon diblock and triblock compounds include those with the general formulas $C_nF_{2n+1}$—$C_mH_{2m+1}$ and $C_nF_{2n+1}C_mH_{2m-1}$, where n=2–12; m=2–16 or $C_pH_{2p+1}$—$C_nF_{2n}$—$C_mH_{2m+1}$, where p=1–12, m=1–12 and n=2–12. Preferred compounds of this type include $C_8F_{17}C_2H_5$, $C_6F_{13}C_{10}H_{21}$, $C_8F_{17}C_8H_{17}$, $C_6F_{13}CH=CHC_6H_{13}$ and $C_8F_{17}CH=CHC_{10}H_{21}$. Substituted ethers or polyethers (i.e. $XC_nF_{2n}OC_mF_{2m}X$, $XCFOC_nF_{2n}OCF_2X$, where n and m=1–4, X=Br, Cl, l or H) and fluorochemical-hydrocarbon ether diblocks or triblocks (i.e. $C_nF_{2n+1}$—O—$C_mH_{2m+1}$, where n=2–10; m=2–16 or $C_pH_{2p+1}$—O—$C_nF_{2n}$—O—$C_mH_{2m+1}$, where p=2–12, m=1–12 and n=2–12) may also used as well as $C_nF_{2n+1}O$—$C_mF_{2m}OC_pH_{2p+1}$, wherein n, m and p are from 1–12. Furthermore, depending on the application, perfluoroalkylated ethers or polyethers may be compatible with the disclosed multiple emulsions.

Polycyclic and cyclic fluorochemicals, such as $C_{10}F_{18}$ (F-decalin or perfluorodecalin) and a mixture of perfluoroperhydrophenanthreneand of perfluoro n-butyldecalin are also within the scope of the invention. Additional useful fluorochemicals include perfluorinated amines, such as F-tripropylamine ("FTPA") and F-tributylamine ("FTBA"). F-4-methyloctahydroquinolizine ("FMOO"), F-N-methyldecahydroisoquinoline ("FMIQ"), F-N-methyldecahydroquinoline ("FHQ"), F-N-cyclohexylpyrrolidine ("FCHP") and F-2-butyltetrahydrofuran ("FC-75"or "FC-77") may also be incorporated. Other contemplated fluorochemicals having nonfluorine substituents, such as, perfluorooctyl hydride, and similar compounds having different numbers of carbon atoms are also useful. Those skilled in the art will further appreciate that other variously modified fluorochemicals are encompassed within the broad definition of fluorocarbons suitable for use in the present invention.

It must be emphasized that any organic hydrogenated compound or agent which may be incorporated into the multiple emulsions as described herein is considered a hydrocarbon for the purposes of the present invention. Hydrocarbon oils are particularly preferred. While the molecular configuration of the selected hydrocarbon is not critical, particularly preferred hydrocarbons will be biocompatible and/or bioactive.

Accordingly, hydrocarbons compatible with the present invention may comprise any organic hydrogenated compound including derivatives thereof. Hydrocarbon compounds compatible with the present invention include saturated or unsaturated hydrocarbons (cyclic, aliphatic or aromatic), or hydrocarbon derivatives including substituted and unsubstituted compounds (e.g. alcohols, aldehydes, ketones, amines, ethers, amides, etc.) Further, the selected hydrocarbon or hydrocarbons may contain a charged substituent. As indicated above, hydrocarbon oils are particularly preferred. Exemplary biocompatible hydrocarbon oils that may be used include naturally occurring oils such as canola oil, safflower oil, soybean oil, olive oil, corn oil, castor oil, sunflower oil and derivatives thereof. Moreover, naturally occurring compounds such as paraffins, waxes, phospholipids, lipids, glycerides and other fatty acid derivatives may be used to form the desired multiple emulsion. For example, triglycerides and, in particular, medium chain triglycerides may be incorporated in the bioactive formulations of the present invention. Furthermore, the selected hydrocarbon may be synthetic or partially synthetic. In addition, mixtures of different hydrocarbons, both bioactive and non-bioactive, may be used.

In addition to the aforementioned components, the multiple emulsions of the present invention further comprises one or more dispersants. Preferably the dispersants will be selected from the group consisting of fluorinated surfactants and non-fluorinated surfactants. Typically, the incorporated dispersant or dispersants, which may be any surfactant, emulsifying agent or mixture thereof, will be largely deposited at the two interfaces between the three distinct phases of the disclosed multiple emulsions. In this position, the selected dispersants act to lower the interfacial tension thereby stabilizing the emulsion. The incorporated dispersant or dispersants are preferably present in concentration of from about 0.001% to about 15% w/w of the emulsion and more preferably from about 0.01% to about 5% w/w.

Those skilled in the art will appreciate that the choice of dispersant will be strongly influenced by the composition of the phases to be stabilized. For example, in a W-in-HC-in-FC multiple emulsion a phospholipid may be used to stabilize the discontinuous emulsified phase comprising a W-in-HC emulsion while a fluorinated diblock compound may be used to stabilize the HC-FC interface. Generally, fluorinated surfactants will be preferred when one of the phases on either side of the first or second interface comprises a fluorocarbon. In particularly preferred embodiments the selected fluorinated surfactant will be soluble or dispersible in the fluorocarbon phase and will exhibit a relatively low hydrophilic-lipophilic balance (HLB). Conversely, for stabilizing emulsions (or parts of multiple emulsions) that do not comprise a fluorocarbon, non-fluorinated surfactants typically having a higher HLB will be preferred. Other embodiments may incorporate natural or synthetic polymers and/or polymeric components (surfactants and non-surfactants, soluble or insoluble) to stabilize the multiple emulsions. In any case, it must be emphasized that both fluorinated and non-fluorinated dispersants, or mixtures thereof, may be used at either interface with any combination of emulsion components as long as they provide the desired stabilization.

Fluorinated dispersing agents or dispersants useful in the present invention include fluorinated surfactants which preferably contain at least four fluorine atoms. These fluorinated surfactants can be of different types. Classes of fluorinated surfactants contemplated for use in the present invention include, for example, amphiphiles containing phosphorus (e.g., (perfluoroalkyl)alkylene mono- or dimorpholinophosphate and fluorinated phospholipids) or alcohols, polyols or polyhydroxylated or aminated derivatives including amine oxides and amino acid derivatives. Such fluorinated surfactants are described, for example, in EP-A-0 255 443, FR-A-2 665 705, FR-A- 2 677 360, FR-A- 2 694 559, FR-A- 2 679 150, WO90/15807 U.S. Pat. No. 3,828,085 and EP-A-0311473 and in "Fluorinated Surfactants Intended for Biomedical Uses", J. Greiner, J. G. Riess and P. Vierling in *Organofluorine Compounds in Medicinal Chemistry and Biomedical Applications*, R. Filler, T. Kobayashi and Y. Yagupolski (eds.), Elsevier, 339–380 (1993) each of which is incorporated herein by reference.

In a particularly preferred embodiment, the multiple emulsions of the present invention comprise a (perfluoroalkyl)alkylene phosphate of the formula:

or

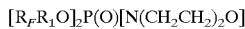

wherein $R_F$ is $CF_3(CF_2)_t$, such that t is from 1 to 11 and $R_1$ is a saturated or unsaturated, linear or branched hydrocarbon chain and both $R_F$ and $R_1$ may contain at least one oxygen and/or sulfur atom.

Other preferred fluorinated surfactants include compounds having at least one fluorinated region and at least one hydrogenated region. For example, hydrogenated/fluorinated compounds of the general formula $R_F$-W-$R_H$ are particularly useful. In such compounds $R_F$ is a linear, branched or cyclic highly fluorinated radical having from about 2 to about 14 carbon atoms and optionally including at least one oxygen atom and/or at least one halogenated substituent; $R_H$ is a linear, branched or cyclic saturated or unsaturated hydrocarbon radical having up to about 18 carbon atoms, optionally containing at least one —O— or —S— group; and W is a single bond, oxygen or sulfur.

In a particularly preferred embodiment, $R_F$ is $CF_3(CF_2)_t$, wherein t is from 1 to 11; W is absent and replaced by a single bond, and $R_H$ is a saturated or unsaturated alkyl group of from 1 to 18 atoms. It will be appreciated that such compounds may preferably be used at a HC-FC interface or in conjunction with a non-fluorinated surfactant (i.e. a phospholipid) at a W-FC interface. Of course, mixtures of fluorinated surfactants are also contemplated. In either case, the use of such compounds can provide the desired reduction of interfacial tension and associated emulsion stability.

Besides the aforementioned fluorinated surfactants, non-fluorinated surfactants may also be incorporated in the disclosed multiple emulsions to lower interfacial tension. As with the fluorinated surfactants, these compounds may be present at either the first interface in the discontinuous emulsified phase or at the second interface between the discontinuous emulsified phase and the continuous hydrophobic phase. Such non-fluorinated surfactants, which may comprise a relatively high HLB, are particularly preferred for the stabilization of HC-W systems whether the HC component is present in the discontinuous emulsified phase or in the continuous hydrophobic phase. Again, mixtures of these dispersants are clearly contemplated as being within the scope of the invention.

Exemplary non-fluorinated surfactants compatible with the teachings herein comprise hydrogenated, non-ionic, anionic, cationic or zwitterionic surfactants. Preferred hydrogenated surfactants include, for example, phospholipids, copolymers of the polyoxyethylenepolyoxypropylene type (e.g., PLURONIC F-68®) and polyoxyethylene sorbitan esters. M particularly, in preferred embodiments the non-fluorinated surfactant is selected from the group consisting of alcohols, salts of fatty acids, phosphatidylcholines, N-monomethyl-phosphatidylethanolamines, phosphatidic acids, phosphatidyl ethanolamines, N,N-dimethyl-phosphatidyl-ethanolamines, phosphatidyl ethylene glycols, phosphatidylmethanols, phosphatidylethanols, phosphatidylpropanols, phosphatidylbutanols, phosphatidylthioethanols, diphytanoyl phosphatides, egg yolk phospholipids, cardiolipins, isomannide monooleates, glycolipids, phosphatidylserines, phosphatidylglycerols and aminoethylphosphonolipids. Preferably, the nonfluorinated surfactant contains at least one mono-unsaturated moiety. In particularly preferred embodiments the nonfluorinated surfactant is 1,2-dioleoylphosphatidic acid or 1,2-dioleoyphosphatidyl ethanolamine.

In selected embodiments the non-fluorinated surfactant may exhibit a low hydrophilic lipophilic balance. Such surfactants include SPANS®, BRIJs®, ethoxylates, dialkyl nonionic surfactants and dialkylzwitterionic surfactants. The multiple emulsion may further comprise a surface active oil capable of decreasing the spontaneous curvature of the surfactant film. Preferably, the surface active oil is a monoglyceride, diglyceride, long-chain alcohol or sterol.

The multiple emulsions of the invention may also comprise one or more additives which are present in either of the components of the discontinuous emulsified phase, in the continuous hydrophobic phase, in all three of the distinct phases, or at the interface between the phases. The additives may include, for example, mineral salts, buffers, oncotic and osmotic agents, nutritive agents, active principles or any other ingredient capable of augmenting the favorable characteristics of the multiple emulsions including their stability, therapeutic efficacy and tolerance.

As discussed above, the multiple emulsions of the present invention are capable of delivering any desired bioactive agent that may be incorporated in either of the components of the discontinuous emulsified phase, the continuous hydrophobic phase or at the interfaces between the three distinct phases. Lipophilic or hydrophilic agents may be combined with the multiple emulsions either prior to, or after, formation. As used herein, the term bioactive agent is defined to mean any pharmaceutical compound or composition, including diagnostic and therapeutic agents as well as physiologically acceptable gases such as oxygen or nitric oxide, which may be administered to an animal to treat a disorder or disease. Insoluble bioactive agents or bioactive agents associated with insoluble polymeric microparticulates are also contemplated. Preferred bioactive agents include hydrophilic drugs with solubility in water and lipophilic drugs. Mixtures of bioactive agents may be delivered in the same or different phases of the multiple emulsions depending on their physical characteristics. For example, a hydrophilic agent may be concentrated in the polar liquid phase while a lipophilic agent may be sequestered in an HC phase present in the discontinuous emulsified phase. Additionally, amphiphilic compounds may be concentrated at one or both of the interfaces. Most preferably, the incorporated bioactive agents are lipophilic agents which are associated with the second component (i.e. HC or FC) in the discontinuous emulsified phase.

It will be appreciated that the selection of compatible bioactive agents, lipophilic, hydrophilic or amphiphilic is limited only by the ability to incorporate them in the multiple emulsions as disclosed in the present invention. In this regard, it will be appreciated that the bioactive agent may be solubilized in one or more phases or be present in a solid particulate form. Yet, some indication as to the ability of an individual bioactive agent to be incorporated as a solute in the non-polar liquid phases of the disclosed preparations may be derived from the measured value of its lipophilicity.

The convention is to measure and report the lipophilicity of a bioactive agent using the log of the octanol/water partition coefficient (Log $P_{o/w}$). In this system increasing lipophilicity corresponds to higher Log $P_{o/w}$ values. Preferably, lipophilic bioactive agents incorporated in the present invention will have a Log $P_{o/w}$ greater than about 0.5. More preferably the incorporated lipophilic bioactive agents will have a Log $P_{o/w}$ greater than about 2.0. As those skilled in the art will appreciate, values such as these indicate that a compound has limited solubility in an aqueous environment.

Preferably, the bioactive multiple emulsions of the present invention incorporate less than about 50% w/v of a therapeutic or diagnostic agent, more preferably less than about 20% and even more preferably less than about 10% w/v. Diagnostic agents will typically be incorporated at higher concentrations while hydrocarbons comprising a bioactive agent may have the concentrations provided above. The precise amount of bioactive agent incorporated in the multiple emulsions of the present invention is dependent upon the agent of choice, the required dose, and the form of the drug actually used for incorporation. Those skilled in the art will appreciate that such determinations may be made using wellknown pharmacological techniques in combination with the teachings herein.

Preferred bioactive agents comprise hydrophilic and lipophilic respiratory agents, bronchodilators, bronchoconstrictors, antibiotics, antivirals, mydriatics, antiglaucomas, anti-inflammatories, antihistaminics, antineoplastics, anesthetics, ophthalmic agents, enzymes, cardiovascular agents, polynucleotides, genetic material, viral vectors, immunoactive agents, imaging agents, immunosuppressive agents, peptides, proteins, physiological gases, gastrointestinal agents and combinations thereof.

Further exemplary embodiments of the present invention comprise anti-inflammatory agents such as the glucocorticosteroids (i.e. cortisone, prednisone, prednisolone, dexamethasone, betamethasone, Beclomethasone diproprionate, Triamcinolone acetonide, Flunisolide), xanthines (i.e. theophylline, caffeine), chemotherapeutics (i.e. cyclophosphamide, lomustine, methotrexate, cisplatin, carboxy platin, taxane derivatives), antibiotics (i.e. aminoglycosides, penicillins, cephalosporins, macolides, quinolones, tetracyclines, chloramphenicol), bronchodilators such as the $B_2$-agonists (i.e. adrenaline, isoprenaline, salmeterol, salbutamol, terbutaline, formoterol) and surfactants. Still other exemplary embodiments include α|β adrenergic blockers (i.e. Normodyne, Trandate), angiotensin converting enzyme inhibitors (i.e. Vasotec), antiarrhythmics, beta blockers, calcium channel blockers, inotropic agents, vasodilators, vasopressors, anesthetics (i.e. morphine) and ophthalmic agents (i.e. Polymyxin B, Neomycin, Gramicidin).

Most preferred agents include glucocorticosteroids, brochodilators, antineoplastic compounds such as taxane derivatives (i.e. Taxol, Taxotere) and the base forms of drugs typically administered as the salt derivative (i.e. Gentamicin, Ciprofloxacin). In accordance with the present invention, those skilled in the art will appreciate that various forms of these compounds, including various pharmaceutically acceptable salts, may be used to modify the therapeutic index of the bioactive agents.

Because the multiple emulsions of the present invention are uniquely suited for various administrative techniques such as ocular, oral, pulmonary, rectal, synovial, subcutaneous, intramuscular, intraperitoneal, nasal, vaginal, or aural administration of medicaments or diagnostic compounds, they are compatible for use with a wide variety of bioactive agents. Accordingly, the foregoing list of compounds is exemplary only and not intended to be limiting. It will also be appreciated by those skilled in the art that the proper amount of bioactive agent and the timing of the dosages may be determined for the formulations in accordance with already-existing information and without undue experimentation.

As previously described, the components discussed above may be combined to provide novel multiple emulsions comprising three distinct phases. Depending on parameters such as formulation, processing and temperature, the multiple emulsions of the present invention may comprise micelles, vesicles or other colloidal aggregates that may compartmentalize at least part of the incorporated bioactive compound. Moreover, in particularly preferred embodiments the preparations of the present invention may be in the form of gels that are relatively effective for topical use. Regardless of the final preparation form, sequestering at least a portion of the bioactive agent in one of the components of the discontinuous emulsified phase will promote extended delivery profiles and more reliable dosing regimens.

The multiple emulsions of the present invention may be formed using a variety of different emulsification processes. It should be emphasized that the order the components are combined, including the bioactive agent or agents, is not critical as long as the desired preparation is produced. Preferably, the multiple emulsions are prepared by initially forming what will become the discontinuous emulsified phase as a conventional or reverse emulsion. Such emulsions may be formed by adding the second component (i.e. FC or HC) to an aqueous dispersion of a fluorinated or non-fluorinated dispersant and emulsifying the resulting mixture.

The resulting homogeneous emulsion may then be added to the hydrophobic continuous phase (i.e. FC or HC) optionally containing a dispersant and the entire mixture emulsified to provide the multiple emulsions of the present invention. In this regard it must be emphasized that the previously formed conventional or reverse emulsion is not destroyed (i.e. it remains a homogeneous dispersion) but rather is dispersed as small discrete droplets in the hydrophobic continuous phase. Accordingly, the energy used in the second step will not be enough to disrupt the emulsion formed in the first step. It will be appreciated that each of the individual droplets of the discontinuous emulsified phase preferably contains discrete droplets of the polar liquid or second component (depending on what type of emulsion was initially formed). Thus, in selected embodiments the multiple emulsions are actually triple emulsions comprising three distinct phases and two distinct interfaces.

It is further within the purview of the present invention to emulsify multiple emulsions (i.e. triple emulsions) in a continuous hydrophobic phase to provide a quadruple multiple emulsion. Such a preparation is discussed in more detail in connection with Example 9 below which describes a preferred gel embodiment. Preferably, the continuous hydrophobic phase (again FC or HC) will comprise a third dispersant which may be the same or different as the first and second dispersants and may be fluorinated or non-fluorinated. The emulsification of the quadruple multiple emulsion may be achieved using conventional techniques well known in the art and the resulting preparation should provide for the compartmentalization of an incorporated bioactive agent. Again, the final emulsifying step should be performed so as not to disrupt the previously formed triple emulsion. As such, the quadruple emulsion having a hydrophobic continuous phase should allow for the effective administration of selected compounds.

As indicated, whatever form the final multiple emulsion takes, conventional emulsification processes may be used during the formation. As will be appreciated by those skilled in the art, emulsification typically requires the input of energy to convert an immiscible two phase system into a substantially homogeneous suspension of discontinuous small droplets. In the present invention, both the formation of the initial emulsion destined to become the discontinuous emulsified phase and the formation of the multiple emulsion may be carried out using techniques such as mechanical stirring, vibration, microfluidization, sonication or homogenization under pressure. Again, it is preferable that the energy imparted to the system during the later emulsification steps is not sufficient to disrupt the previously formed emulsions. Thus, in some cases, the multiple emulsions can be formed by mixing with a relatively gentle vortex which is particularly preferable when incorporating a drug that is subject to disruption (i.e. a protein or nucleic acid). In addition, dispersion of the hydrocarbon, polar liquid or fluorochemical may, depending on the components, concentration, and emulsification step (i.e. first or second) occur spontaneously upon addition of the dispersing agent.

The discontinuous emulsified phase of the disclosed multiple emulsions preferably comprises relatively small particulates (or droplets) having an average diameter on the order of nanometers to tens of microns though preferably less than 100 $\mu$m. In preferred embodiments the discontinuous emulsified phase comprises particulates having an average diameter on the order of from about 1 $\mu$m to about 10 $\mu$m and more preferably about 5 $\mu$m. As used herein, the terms "particles" or "particulates" refer to the emulsion droplets of the discontinuous phase. The discontinuous emulsified phase, in turn, contains smaller particulates comprising the dispersed polar liquid or second component. Preferably, the particulates contained in the dicontinuous emulsified phase have an average diameter on the order of from about 0.1 $\mu$m to about 5 $\mu$m and more preferably in the range of about 0.5 $\mu$m to about 2 $\mu$m.

As previously indicated, the presence of such small, evenly distributed particles can greatly increase the bioavailability of any incorporated bioactive agents (particularly lipophilic agents) at the physiological target site due to their relatively large surface area and effective encapsulation of the therapeutic or diagnostic compound. Moreover, by altering the component concentration, preparation conditions or amount of energy imparted during emulsification, the size of the incorporated particulates may be controlled. Those skilled in the art will appreciate that the ability to control the incorporated particle size may be used to attenuate and extend drug delivery profiles to optimize dosing regimes.

With respect to the prepared multiple emulsions, the final concentration of the components may be varied as needed to provide preparations having the desired properties. Moreover, the concentration of the individual components will vary based on whether they are used in the discontinuous emulsified phase or in the continuous phase. However, in preferred embodiments the disclosed emulsions may, for example, comprise 0.1% up to 49% v/v of a second component present in the emulsified discontinuous phase; from about 5% up to about 50% v/v of a polar liquid present in the emulsified discontinuous phase; from about 5% up to about 99% v/v of a continuous hydrophobic phase. In addition to the aforementioned components, preferred embodiments of the multiple emulsions may further comprise from about 0.0001% to about 20% w/w of one or more dispersants and up to about 50% w/w of one or more bioactive agents although preferably the selected bioactive agent or agents will comprise from about 0.1% to about 10% w/w.

It will further be appreciated that the multiple emulsions of the present invention can be administered via several different routes, depending upon the indication to be treated. For example, intranasal or intrapulmonary administration is contemplated for the treatment of respiratory or systemic disorders. An example would include the treatment of lung cancer or other systemic cancers with taxane derivatives by administration through the pulmonary air passages. Use of FC continuous phase multiple emulsions is particularly preferred for pulmonary administration. Intraperitoneal, subcutaneous and ocular administration of the emulsions are also contemplated as well as administration in any other body cavity. The multiple emulsions of the invention may also be used to deliver therapeutic and diagnostic agents to the gastrointestinal tract by, for example, the oral route of administration. A contemplated example would be the delivery of antibiotics to the lining of the gastrointestinal tract in the treatment of *Heliobacter pylon* infections. *H. pylori* has been implicated in the cause of gastric ulcers and stomach cancer. Antibiotics effective in the treatment of *H. pylori* infections could be administered in the form of a multiple emulsion.

It will also be appreciated by those skilled in the art that the emulsions of the present invention may be sterilized, for example, by heat, irradiation, ultrafiltration or combinations of any of these or equivalent techniques. Specifically, the multiple emulsions of the invention may be sterilized, for example, by autoclaving at 121° C. for 15 minutes or by filtration through a 0.22 $\mu$m filter.

The high bioavailability bioactive preparations of the present invention may advantageously be supplied to the physician in a sterile prepackaged form. More particularly, the formulations may be supplied as stable, preformed multiple emulsions, ready for administration or as separate, ready to mix components. When supplied as components the final preparation of the multiple emulsion could easily be performed in the pharmacy just prior to administration.

In any case the following nonlimiting examples of various formulations of the present invention illustrate exemplary methods for the their formation and resultant characteristics.

For each of the following examples milky emulsions were obtained. Larger globules or particulates (i.e. the discontinuous emulsified phase) containing tiny droplets were visualized by optical microscopy. The average sizes of the globules varied from $3_{10}$ $\mu$m, as assessed by photosedimentation. Most of the exemplary multiple emulsions were heated at 121° C. for 15 min in an autoclave. The average size of the discontinuous emulsified phase particulates were measured immediately after heating and after one month storage at 25° C.

EXAMPLE 1

Dodecane-in-Water-in-Perfluorooctyl Bromide

Multiple Emulsion

A two step procedure was followed to form a dodecane-in-water-in-Perfluorooctyl bromide multiple emulsion in accordance with the present invention:

a) Preparation of the HC-in-W emulsion 15 mL of dodecane (30% v/v) was added dropwise into 32.5 mL (65% v/v) of an aqueous dispersion of natural egg yolk phospholipids (2.5 g, 5% v/v). A coarse premix was obtained using an Ultra-Turrax mixer. Further homogenization using a Microfluidizer (10 passes, 10,000 psi) yielded a hydrocarbon-in-water emulsion. The average particle size was 0.25 µm as measured by photosedimentation (Horiba Capa-700).

b) Preparation of the HC-in-W-in-FC Multiple Emulsion

A 2% w/v concentrated solution of the fluorinated surfactant perfluorooctyl(undecyl)dimorpholinophosphate $[C_8F_{17}(CH_2)_{11}OP(O)[N(CH_2CH_2)_2O]_2$ (F8C11DMP)] in perfluorooctyl bromide was prepared. 10 ml of the hydrocarbon-in-water emulsion obtained as described above was then added dropwise to 80 mL of the fluorinated surfactant-containing fluorocarbon solution while stirring vigorously. The obtained dispersion was then emulsified by mixing in an Ultra-Turrax mixer. An emulsion was obtained with an average particle size of 5.5 µm (photosedimentation).

As the resulting multiple emulsion was readily diluted with a fluorocarbon, but not with a hydrocarbon or water, the continuous phase was fluorinated. As visualized by optical microscopy, the discontinuous emulsified phase was made up of particulates (a few microns in diameter) containing smaller droplets (<1 µm). After four months of storage at 25° C., creaming was noticed, but the preparation could readily be re-homogenized by simple hand shaking to provide an average particulate size of approximately 6.2 µm.

EXAMPLE 2

Castor oil-in-Water-in-Perfluorooctyl Bromide

Multiple Emulsion

A two step procedure similar to that used in example 1 was used to form a castor oil-in-water-in-perfluorooctyl bromide (3.2/16.1/80.6% v/v) multiple emulsion:

0.2 mL of castor oil (Fluka) was added dropwise into 1.0 mL of an aqueous dispersion of natural egg yolk phospholipids (0.1g). A coarse premix was obtained using an Ultra-Turrax mixer. Further homogenization using an Emulsiflex B3 device yielded a castor oil-in-water emulsion. This emulsion was then added dropwise with vigorous stirring to a fluorocarbon solution (5 mL) comprising F8C11DMP (0.1 g) in perfluorooctyl bromide. The resulting dispersion was then homogenized by mixing with an Ultra-Turrax mixer to provide a milky emulsion. As visualized by optical microscopy, the discontinuous emulsified phase was made up of irregularly-shaped particles containing tiny droplets. Average particle sizes (photosedimentation) were: initial: 7.5±0.5 µm, after one month: 7.8±0.5 µm.

EXAMPLE 3

Isopropyl myristate-in-Water-in-APF-240

Multiple Emulsion

A two step procedure similar to that used in example 1 was used to form an isopropyl myristate-in-water-in-APF-240 (6.1/18.2/75.7% v/v) multiple emulsion:

0.4 mL of isopropyl myristate (Sigma) was added dropwise into 1.2 mL of an aqueous dispersion of Pluronic F-68 (0.1 g). A coarse premix was obtained using an Ultra-Turrax mixer. Further homogenization using an Emulsiflex B3 device yielded an isopropyl myristate-in-water emulsion having a 100 nm average particle size, as assessed by laser light scattering. This emulsion was then added dropwise with vigorous stirring to a fluorocarbon phase (5 mL) consisting of a dispersion of F8C11DMP (0.1 g) in APF-240. The resulting mixture was then homogenized using an Ultra-Turrax mixer to provide a milky emulsion. Inspection by optical microscopy revealed that the discontinuous emulsified phase consisted of spherical particles containing tiny droplets. Average particle sizes (photosedimentation) were: initial: 8.2±0.5 µm, after one month: 8.5±0.5 µm.

EXAMPLE 4

Dodecane-in-Water-in-Perfluorooctyl Bromide

Multiple Emulsion

A Dodecane-in-water-in-perfluorooctyl bromide multiple emulsion (15.4/7.7/76.9/% v/v) was prepared as follows: 1 mL of dodecane was added dropwise into 0.5 mL of an aqueous dispersion of natural phospholipids (0.03 g). A coarse premix was obtained using an Ultra-Turrax mixer. The premix was then subject to homogenization using an Emulsiflex B3 device which yielded a dodecane-in-water emulsion. This emulsion was then added dropwise with vigorous stirring to a fluorocarbon phase (5 mL) comprising a dispersion of F8C11DMP (0.1 g) in perfluorooctyl bromide. The resulting dispersion homogenized using an Ultra-Turrax mixer to provide a milky emulsion. Observation by optical microscopy revealed that the discontinuous emulsified phase consisted of spherical particles containing tiny droplets. Average particle sizes (photosedimentation) were: initial: 4.1±0.5 µm, after one month: 6.3±0.5 µm.

EXAMPLE 5

Squalane-in-Water-in-Perfluorooctyl Bromide

Multiple Emulsion

A hydrocarbon-in-water-in-fluorocarbon (HC/W/FC) emulsion containing 8% v/v of squalane, 20% v/v of water and 72% v/v of perfluorooctyl bromide was prepared as follows. The emulsion was stabilized by Pluronic® F-68 and a fluorinated surfactant with a dimorpholinophosphase head group (F8C11DMP).

20 mg of Pluronic F-68 was solubilized in 0.5 ml of water (0.9% NaCl). 0.2 mL of squalane is added to the Pluronic solution. The mixture was dispersed by vortexing for 3 min yielding a viscous hydrocarbon-in-water (HC-in-W) emulsion.

54 mg of F8C11DMP was dissolved in 1.8 mL of perfluorooctyl bromide by heating. A transparent solution of the fluorinated surfactant in fluorocarbon was obtained. The previously obtained HC-in-W emulsion was added dropwise to the surfactant-fluorocarbon solution while vortexing the mixture for 10 min. A hydrocarbon-in-water-in-fluorocarbon emulsion was thereby obtained.

The resulting multiple emulsion was white and fluid in appearance. The emulsion could be diluted in perfluorooctyl bromide, but not in squalane or in water indicating that the continuous phase comprises a fluorocarbon. Optical microscopy revealed a discontinuous emulsified phase comprising particles containing smaller droplets dispersed in the fluorocarbon continuous phase. The mean particle size was 2.7 microns. The emulsion was stable for at least 2 months at room temperature.

EXAMPLE 6

Squalane-in-Water-in-Perfluorooctyl Bromide

Multiple Emulsion

A hydrocarbon-in-water-in-fluorocarbon(HC/W/FC) emulsion containing 2.55% v/v of squalane, 7% v/v of water and 90.45% v/v of perfluorooctyl bromide was formed as follows. The multiple emulsion, which differs from that of the preceding example in component concentration, was stabilized by Pluronic® F-68 and a fluorinated surfactant.

20 mg of Pluronic F-68 was solubilized in 0.5 mL of water (0.9% NaCl). 0.2 mL of squalane was then added to the Pluronic solution. The mixture was dispersed by vortexing for 3 min to provide a viscous hydrocarbon-in-water emulsion.

54 mg of F8C11DMP was dissolved in 1.8 mL of perfluorooctyl bromide by heating to provide a transparent solution of fluorinated surfactant in fluorocarbon. The HC/W emulsion (0.2 mL) was added dropwise to the surfactant-in-fluorocarbon solution while vortexing the mixture for 10 min. A milky white hydrocarbon-in-water-in-fluorocarbonemulsion was obtained.

The resulting emulsion was capable of being diluted in perfluorooctyl bromide but not in squalane or in water indicating that the continuous phase is formed by the fluorocarbon. Optical microscopy revealed a discontinuous emulsified phase comprising particles containing smaller droplets dispersed in the fluorocarbon continuous phase. The mean particle size of the discontinuous phase was approximately 2.5 microns with the emulsion being stable for at least one month at room temperature.

EXAMPLE 7

Squalane-in-Water-in-Perfluorooctyl Bromide

Multiple Emulsion

A squalane-in-water-in-perfluorooctyl bromide (8/20/72% v/v) multiple emulsion was formed as follows. The emulsion differs from that set forth in Example 5 in that a different fluorinated surfactant is used for stabilization.

20 mg of Pluronic F-68 was solubilized in 0.5 mL of water (0.9% NaCl). 0.2 mL of squalane was then added to the Pluronic solution. The mixture was dispersed by vortexing for 3 min to provide a viscous hydrocarbon-in-water emulsion.

54 mg of the mixed fluorinated/hydrogenated surfactant of the glycolipid type Gal-O—CH[CH(OH)(CH$_2$OH)]. [(CHOH)$_2$]C(O)NHCH$_2$C(O)NHCH[(CH$_2$)$_8$CH=CH$_2$] [(CH$_2$)$_2$C$_8$F$_{17}$] was dissolved in 1.8 mL of perfluorooctyl bromide by heating to provide a transparent solution comprising surfactant and fluorocarbon. The previously obtained hydrocarbon-in-water emulsion was added dropwise to the fluorocarbon solution while vortexing the mixture for 10 min.

A slightly viscous, white hydrocarbon-in-water-in-fluorocarbon emulsion was obtained. Optical microscopy revealed a multiple emulsion comprising a discontinuous emulsified phase of particles containing smaller droplets dispersed in the fluorocarbon continuous phase. The emulsion was stable for at least 4 months at room temperature.

EXAMPLE 8

Preparation of a HC-in-W-in-FC Multiple Emulsion

Comprising a Bioactive Agent

A squalane-in-water-in-perfluorooctyl bromide (8/20/72% v/v) multiple emulsion comprising DNA that expresses the antigen of hepatitis B was prepared as follows:

A DNA dispersion was prepared by dispersing 2.4 mg of DNA in 1 mL of water for injection (0.9% NaCl) followed by subsequent dilution in 3 mL of water for injection in a sterile hood. 1 mL of the DNA dispersion was then added to 40 mg of Pluronic F-68 with vortexing to provide a clear dispersion. 0.4 mL of squalane was then added dropwise using a sterile syringe. The mixture was dispersed by vortexing for 3 min to provide a viscous HC-in-W emulsion comprising a bioactive agent.

108 mg of a fluorinated surfactant (F8C11DMP) was then solubilized in 3.6 mL of perfluorooctyl bromide with mild heating to give a transparent solution. The DNA containing HC-in-W emulsion was added dropwise to the fluorocarbon/surfactant solution while vortexing for 10 min. to provide a white hydrocarbon-in-water-in-fluorocarbon multiple emulsion. It was found that the multiple emulsion could be diluted in perfluorooctyl bromide though not in squalane or in water, thereby indicating that the continuous phase comprised a fluorocarbon. Optical microscopy revealed a discontinuous emulsion comprising a discontinuous emulsified phase dispersed in a continuous fluorocarbon phase. This emulsion was stable for at least 5 months at 4° C.

EXAMPLE 9

Preparation of a HC-in-(FC-in-W)-in-FC Quadruple Emulsion

A dodecane-in-(APF-240-in-water gel)-in-perfluorooctyl bromide quadruple emulsion was prepared as follows:

0.2 mL of dodecane was added dropwise under agitation to 1.0 mL of a soft gel with a water continuous phase which consisted of 90% w/w of APF-240. The gel further comprised approximately 10% w/w of water and approximately 0.5% of a fluorinated amine oxide, $C_7F_{15}C(O)NH(CH_2)_2N(O)(CH_3)_2$.

Homogenization of the resulting mixture using an Ultra-Turrax mixer provided a dodecane-in-(APF-240-in-water gel) emulsion. This viscous emulsion was then added dropwise, with vigorous stirring, to a fluorocarbon solution (5 mL) comprising F8C11DMP (0.1 g) in perfluorooctyl bromide. The resulting dispersion was then homogenized using an Ultra-Turrax mixer to provide a milky white multiple emulsion.

Optical microscopy revealed a discontinuous emulsified phase comprising particulates containing tiny droplets in a continuous hydrophobic phase. Average particle sizes (photosedimentation) were initially 5.1±0.5 μm with an increase after one month to approximately 10.1±0.5 μm.

EXAMPLE 10

Water-in-Dodecane-in-Perfluorooctyl Bromide Multiple Emulsion

A water-in-dodecane-in-perfluorooctyl bromide (5.7/8.6/85.7% v/v) multiple emulsion was prepared as follows:

2 mL of water was added dropwise to 3 mL of dodecane containing span 80 (0.05 g) while mixing with an Ultra- Turrax mixer to provide a water-in-dodecane reverse emulsion. 0.5 ml of this emulsion was added dropwise to 3 ml of a fluorocarbon solution comprising F8C11DMP (0.05 g) in perfluorooctyl bromide. The resulting dispersion was then homogenized using an Ultra-Turrax mixer to provide a milky emulsion.

Optical microscopy revealed the presence of a discontinuous emulsified phase comprising particles containing tiny droplets. The average particle size (photosedimentation) was initially about 3.2±0.5 µm and increased to approximately 8.3±0.5 µm.

EXAMPLE 11

Water-in-hexadecane-in-APF-240

Multiple Emulsion

A water-in-hexadecane-in-APF-240 (10/4.3/85.7% v/v) multiple emulsion was prepared as follows:

3.5 mL of water was dispersed in 1.5 mL of hexadecane containing span 80 (0.1 g) using an Ultra-Turrax mixer to provide a water-in-hexadecane emulsion. This emulsion (0.5 mL) was then added dropwise to a fluorocarbon solution (3 mL) comprising $C_6F_{13}C_{10}H_{21}$ (0.025 g) in APF-240. The resulting dispersion was homogenized using an Ultra-Turrax mixer to provide a milky emulsion.

Optical microscopy revealed a discontinuous emulsified phase comprising particles containing tiny droplets. Average particle size (photosedimentation) were initially about 2.8±0.5 µm increasing to about 4.1±0.5 µm after one month.

EXAMPLE 12

Water-in-APF-240-in-Hexadecane

Multiple Emulsion

A water-in-APF-240-in-hexadecane emulsion (10/4.3/85.7% v/v) multiple emulsion having a mixture of fluorinated dispersants was prepared as follows:

3.5 mL of water was dispersed in 1.5 mL of APF-240 containing F8C11DMP (0.1 g) and $C_6F_{13}C_{10}H_{21}$ (0.025 g) using an Ultra-Turrax mixer to provide a water-in-APF-240 emulsion. This emulsion (0.5 mL) was added dropwise to hexadecane (3 mL) containing span 80 (0.1 g). The resulting dispersion was homogenized using a Ultra-Turrax mixer to provide a milky emulsion.

Examination by optical microscopy revealed a discontinuous emulsified phase comprising particulates containing tiny droplets. The initial average particle size (photosedimentation) was 6.2±0.5 µm.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A stable multiple emulsion for the delivery of bioactive agents comprising:
 a discontinuous emulsified phase comprising a first dispersant, a polar liquid and a second component selected from the group consisting of fluorocarbons and hydrocarbon oils wherein the second component is dispersed in the polar liquid or the polar liquid is dispersed in the second component;
 a continuous phase comprising a hydrophobic compound; and
 an effective dispersing amount of a second dispersant wherein said discontinuous emulsified phase is immiscible in said hydrophobic compound.

2. The multiple emulsion of claim 1 wherein said hydrophobic compound is selected from the group consisting of hydrocarbons and fluorocarbons.

3. The multiple emulsion of claim 2 wherein said hydrophobic compound is a fluorocarbon selected from the group consisting of perfluoroalkanes, fluorinated cyclic compounds, halogenated fluorochemicals, fluorinated alkenes, fluorinated ethers, fluorinated polyethers, fluorinated amines, fluorinated hydrides and derivatives thereof.

4. The multiple emulsion of claim 2 wherein said hydrophobic compound is a hydrocarbon selected from the group consisting of saturated hydrocarbons, unsaturated hydrocarbons, lipids, triglycerides, natural oils, synthetic oils and derivatives thereof, said natural oils selected from the group consisting of canola oil, soybean oil, olive oil, corn oil, castor oil, sunflower oil, safflower oil and derivatives thereof.

5. The multiple emulsion of claim 1, wherein said first dispersant or said second dispersant is selected from the group consisting of fluorinated surfactants, fluorocarbon-hydrocarbon diblock compounds and combinations thereof.

6. The multiple emulsion of claim 1, wherein said first dispersant or said second dispersant is selected from the group consisting of a diblock compound selected from the group consisting of compounds having the formula $C_nF_{2n+1}C_mH_{2m+1}$, compounds having the formula $C_nF_{2n+1}C_mH_{2m-1}$ and combinations thereof, wherein n is an integer from 2 to 12 and m is an integer from 2 to 16 and a fluorinated surfactant selected from the group consisting of compounds having the formula $R_FR_1OP(O)[N(CH_2CH_2)_2O]_2$, compounds having the formula $[R_FR_1O]_2P(O)[N(CH_2CH_2)_2O]$ and combinations thereof wherein $R_F$ is $CF_3(CF_2)_t$, such that t is from 1 to 11 and $R_1$ is saturated or unsaturated, linear or branched hydrocarbon chain and both $R_F$ and $R_1$ may contain at least one oxygen and/or sulfur atom.

7. The multiple emulsion of claim 1, wherein said first dispersant or said second dispersant is a non-fluorinated surfactant is selected from the group consisting of alcohols, salts of fatty acids, phosphatidylcholines, N-monomethyl-phosphatidylethanolamines, phosphatidic acids, phosphatidyl ethanolamines, N,N-dimethyl-phosphatidyl-ethanolamines, phosphatidyl ethylene glycols, phosphatidylmethanols, phosphatidylethanols, phosphatidylpropanols, phosphatidylbutanols, phosphatidylthioethanols, diphytanoyl phosphatides, egg yolk phospholipids, cardiolipins, isomannide monooleates, glycolipids, phosphatidylserines, phosphatidylglycerols, aminoethylphosphonolipids and combinations thereof.

8. The multiple emulsion of claim 1, wherein said multiple emulsion is selected from the group consisting of W-in-FC-in-HC emulsions, FC-in-W-in-HC emulsions, W-in-HC-in-FC emulsions and HC-in-W-in-FC emulsions.

9. The multiple emulsion of claim 1 further comprising at least one bioactive agent.

10. The multiple emulsion of claim 9, wherein said bioactive agent is selected from the group consisting of respiratory agents, bronchodilators, bronchoconstrictors, antibiotics, antivirals, mydriatics, antiglaucomas, anti-inflammatories, antihistaminics, antineoplastics, anesthetics, ophthalmic agents, enzymes, cardiovascular agents, polynucleotides, genetic material, viral vectors, immunoactive agents, imaging agents, immunosuppressive agents, peptides, proteins, physiological gases, gastrointestinal agents and combinations thereof.

11. A method for forming a stable multiple emulsion comprising the steps of:
   emulsifying a first dispersant a polar liquid and a second component selected from the group consisting of fluorocarbons and hydrocarbons wherein the second component is dispersed in the polar liquid or the polar liquid is dispersed in the second component to provide an emulsified disperse phase; and
   dispersing said emulsified disperse phase in a continuous phase comprising a hydrophobic compound and a second dispersant wherein said emulsified disperse phase is immiscible in said hydrophobic compound.

12. The method of claim 11 wherein said hydrophobic compound is selected from the group consisting of hydrocarbons and fluorocarbons.

13. The method of claim 12 wherein said hydrophobic compound is a fluorocarbon selected from the group consisting of perfluoroalkanes, fluorinated cyclic compounds, halogenated fluorochemicals, fluorinated alkenes, fluorinated ethers, fluorinated polyethers, fluorinated amines, fluorinated hydrides and derivatives thereof.

14. The method of claim 12 wherein said hydrophobic compound is a hydrocarbon selected from the group consisting of saturated hydrocarbons, unsaturated hydrocarbons, lipids, triglycerides, natural oils, synthetic oils and derivatives thereof, said natural oils selected from the group consisting of canola oil, soybean oil, olive oil, corn oil, castor oil, sunflower oil, safflower oil and derivatives thereof.

15. The method of claim 11, wherein said first dispersant or said second dispersant is selected from the group consisting of fluorinated surfactants, fluorocarbon-hydrocarbon diblock compounds and combinations thereof.

16. The method of claim 11, wherein said first dispersant or said second dispersant is selected from the group consisting of a diblock compound selected from the group consisting of compounds having the formula $C_nF_{2n+}C_mH_{2m+}$, compounds having the formula $C_nF_{2n+}C_mH_{2m-1}$ and combinations thereof, wherein n is an integer from 2 to 12 and m is an integer from 2 to 16 and a fluorinated surfactant selected from the group consisting of compounds having the formula $R_FR_1OP(O)[N(CH_2CH_2)_2O]_2$, compounds having the formula $[R_FR_1O]_2P(O)[N(CH_2CH_2)_2O]$ and combinations thereof wherein $R_F$ is $CF_3(CF_2)_t$, such that t is from 1 to 11 and $R_1$ is a saturated or unsaturated, linear or branched hydrocarbon chain and both $R_F$ and $R_1$ may contain at least one oxygen and/or sulfur atom.

17. The method of claim 11, wherein said first dispersant or said second dispersant is a non-fluorinated surfactant is selected from the group consisting of alcohols, salts of fatty acids, phosphatidylcholines, N-monomethyl-phosphatidylethanolamines, phosphatidic acids, phosphatidyl ethanolamines, N,N-dimethyl-phosphatidyl-ethanolamines, phosphatidyl ethylene glycols, phosphatidylmethanols, phosphatidylethanols, phosphatidylpropanols, phosphatidylbutanols, phosphatidylthioethanols, diphytanoyl phosphatides, egg yolk phospholipids, cardiolipins, isomannide monooleates, glycolipids, phosphatidylserines, phosphatidylglycerols, aminoethylphosphonolipids and combinations thereof.

18. The method of claim 11, wherein said multiple emulsion is selected from the group consisting of W-in-FC-in-HC emulsions, FC-in-W-in-HC emulsions, W-in-HC-in-FC emulsions and HC-in-W-in-FC emulsions.

19. The method of claim 1 further comprising the step of combining at least one bioactive agent with said multiple emulsion.

20. The method of claim 19 wherein said bioactive agent is selected from the group consisting of respiratory agents, bronchodilators, bronchoconstrictors, antibiotics, antivirals, mydriatics, antiglaucomas, anti-inflammatories, antihistaminics, antineoplastics, anesthetics, ophthalmic agents, enzymes, cardiovascular agents, polynucleotides, genetic material, viral vectors, immunoactive agents, imaging agents, immunosuppressive agents, peptides, proteins, physiological gases, gastrointestinal agents and combinations thereof.

21. A method for delivering a bioactive agent to a patient in need thereof comprising:
   providing a bioactive emulsion comprising a discontinuous emulsified phase having therein a first dispersant, a polar liquid and a second component selected from the group consisting of fluorocarbons and hydrocarbons wherein the second component is dispersed in the polar liquid or the polar liquid is dispersed in the second component, said emulsified phase dispersed in a continuous phase comprising a hydrophobic compound and an effective dispersing amount of a second dispersant wherein said emulsified disperse phase is immiscible in said hydrophobic compound and wherein said bioactive multiple emulsion further comprises at least one bioactive agent; and
   administering said bioactive multiple emulsion to a patient.

22. The method of claim 21 wherein said hydrophobic compound is selected from the group consisting of hydrocarbons and fluorocarbons.

23. The method of claim 22 wherein said hydrophobic compound is a fluorocarbon selected from the group consisting of perfluoroalkanes, fluorinated cyclic compounds, halogenated fluorochemicals, fluorinated alkenes, fluorinated ethers, fluorinated polyethers, fluorinated amines, fluorinated hydrides and derivatives thereof.

24. The method of claim 22 wherein said hydrophobic compound is a hydrocarbon selected from the group consisting of saturated hydrocarbons, unsaturated hydrocarbons, lipids, triglycerides, natural oils, synthetic oils and derivatives thereof, said natural oils selected from the group consisting of canola oil, soybean oil, olive oil, corn oil, castor oil, sunflower oil, safflower oil and derivatives thereof.

25. The method of claim 21, wherein said first dispersant or said second dispersant is selected from the group consisting of fluorinated surfactants, fluorocarbon-hydrocarbon diblock compounds and combinations thereof.

26. The method of claim 21, wherein said first dispersant or said second dispersant is selected from the group consisting of a diblock compound selected from the group consisting of compounds having the formula $C_nF_{2n+1}C_mH_{2m+1}$, compounds having the formula $C_nF_{2n+1}C_mH_{2m-1}$ and combinations thereof, wherein n is an integer from 2 to 12 and m is an integer from 2 to 16 and a fluorinated surfactant selected from the group consisting of compounds having the formula $R_FR_1OP(O)[N(CH_2CH_2)_2O]_2$, compounds having the formula $[R_FR_1O]_2P(O)[N(CH_2CH_2)_2O]$ and combinations thereof wherein $R_F$ is $CF_3(CF_2)_t$, such that t is from 1 to 11 and $R_1$ is a saturated or unsaturated, linear or branched hydrocarbon chain and both $R_F$ and $R_1$ may contain at least one oxygen and/or sulfur atom.

27. The method of claim 21, wherein said first dispersant or said second dispersant is a non-fluorinated surfactant is selected from the group consisting of alcohols, salts of fatty acids, phosphatidylcholines, N-monomethyl-phosphatidylethanolamines, phosphatidic acids, phosphatidyl ethanolamines, N,N-dimethyl-phosphatidyl-ethanolamines, phosphatidyl ethylene glycols, phosphatidylmethanols, phosphatidylethanols, phosphatidylpropanols, phosphatidylbutanols, phosphatidylthioethanols, diphytanoyl phosphatides, egg yolk phospholipids, cardiolipins, isomannide monooleates, glycolipids, phosphatidylserines, phosphatidylglycerols, aminoethylphosphonolipids and combinations thereof.

28. The method of claim 21, wherein said multiple emulsion is selected from the group consisting of W-in-FC-in-HC emulsions, FC-in-W-in-HC emulsions, W-in-HC-in-FC emulsions and HC-in-W-in-FC emulsions.

29. The method of claim 21, wherein said bioactive agent is selected from the group consisting of respiratory agents, bronchodilators, bronchoconstrictors, antibiotics, antivirals, mydriatics, antiglaucomas, anti-inflammatories, antihistaminics, antineoplastics, anesthetics, ophthalmic agents, enzymes, cardiovascular agents, polynucleotides, genetic material, viral vectors, immunoactive agents, imaging agents, immunosuppressive agents, peptides, proteins, physiological gases, gastrointestinal agents and combinations thereof.

30. The method of claim 21, wherein said administrating step comprises an administration technique selected from the group consisting of ocular, oral, pulmonary, rectal, synovial, subcutaneous, intramuscular, intraperitoneal, nasal, vaginal, aural and topical.

* * * * *